(12) United States Patent
Kubota

(10) Patent No.: US 9,675,666 B2
(45) Date of Patent: Jun. 13, 2017

(54) IMMEDIATE-RELEASE TABLET FORMULATION, COMPOSITION FOR TABLETS AND METHOD FOR MANUFACTURING IMMEDIATE-RELEASE TABLET FORMULATION

(71) Applicant: ASAHI CALPIS WELLNESS CO., LTD., Tokyo (JP)

(72) Inventor: Akira Kubota, Sagamihara (JP)

(73) Assignee: ASAHI CALPIS WELLNESS CO., LTD., Tokyo (JP)

( * ) Notice: Subject to any disclaimer, the term of this patent is extended or adjusted under 35 U.S.C. 154(b) by 0 days.

(21) Appl. No.: 15/315,805

(22) PCT Filed: Jun. 3, 2015

(86) PCT No.: PCT/JP2015/066011
§ 371 (c)(1),
(2) Date: Dec. 2, 2016

(87) PCT Pub. No.: WO2015/186729
PCT Pub. Date: Dec. 10, 2015

(65) Prior Publication Data
US 2017/0100457 A1    Apr. 13, 2017

(30) Foreign Application Priority Data

Jun. 3, 2014 (JP) .................................. 2014-115327
Dec. 25, 2014 (JP) .................................. 2014-261582

(51) Int. Cl.
| A61K 9/14 | (2006.01) |
| A61K 31/337 | (2006.01) |
| A61K 38/17 | (2006.01) |
| A61K 9/20 | (2006.01) |
| A61K 38/01 | (2006.01) |

(52) U.S. Cl.
CPC ........ *A61K 38/1709* (2013.01); *A61K 9/2013* (2013.01); *A61K 9/2072* (2013.01); *A61K 9/2095* (2013.01); *A61K 38/018* (2013.01)

(58) Field of Classification Search
None
See application file for complete search history.

(56) References Cited

U.S. PATENT DOCUMENTS

| 6,171,619 B1 | 1/2001 | Fusejima et al. |
| 2003/0137067 A1 | 7/2003 | Cooper et al. |
| 2004/0258626 A1 | 12/2004 | Zeng |
| 2005/0158248 A1 | 7/2005 | Zeng |
| 2007/0299014 A1 | 12/2007 | Yamamoto et al. |
| 2009/0004170 A1 | 1/2009 | Ikehara et al. |
| 2009/0264389 A1 | 10/2009 | Zeng |
| 2012/0065175 A1 | 3/2012 | Zeng |

FOREIGN PATENT DOCUMENTS

| EP | 2 725 105 A1 | 4/2014 |
| JP | 10-59842 A | 3/1998 |
| JP | 10-139659 A | 5/1998 |
| JP | 2006-516531 A | 7/2006 |
| JP | 2008-24662 A | 2/2008 |
| JP | 2012-217442 A | 11/2012 |
| JP | 2013-5763 A | 1/2013 |
| JP | 2013-209422 A | 10/2013 |
| WO | 2004/017914 A2 | 3/2004 |
| WO | 2005/012542 A1 | 2/2005 |
| WO | 2009/001787 A1 | 12/2008 |

OTHER PUBLICATIONS

International Searching Authority, International Search Report for PCT/JP2015/066011 dated Aug. 25, 2015.

*Primary Examiner* — Robert A Wax
*Assistant Examiner* — Randeep Singh
(74) *Attorney, Agent, or Firm* — Sughrue Mion, PLLC

(57) ABSTRACT

There are provided a tablet-form immediate-release preparation that contains a high concentration of a casein and/or a casein hydrolysate as an active ingredient but has an excellent physical strength, a composition for the preparation that has an excellent tabletability, and a method for producing the preparation from the composition. Each of the preparation and the composition contains 50% by mass or more of the casein and/or the casein hydrolysate, and further contains a lactose having a volume average particle diameter of not less than 50 μm and not more than 300 μm. The content of the lactose is 6.0 to 100 parts by mass per 100 parts by mass of the casein and/or the casein hydrolysate. The method for producing the preparation contains the steps of: preparing a mixture as the composition; filling a mortar with the mixture and tableting the mixture; and separating the tableted mixture from the mortar.

13 Claims, No Drawings

IMMEDIATE-RELEASE TABLET FORMULATION, COMPOSITION FOR TABLETS AND METHOD FOR MANUFACTURING IMMEDIATE-RELEASE TABLET FORMULATION

CROSS REFERENCE TO RELATED APPLICATIONS

This application is a National Stage of International Application No. PCT/JP2015/066011 filed Jun. 3, 2015, claiming priority based on Japanese Patent Application Nos. 2014-115327 filed Jun. 3, 2014 and 2014-261582 filed Dec. 25, 2014, the contents of all of which are incorporated herein by reference in their entirety.

FIELD OF ART

The present invention relates to a tablet-form immediate-release preparation that contains 50% by mass or more of a casein and/or a casein hydrolysate and has an appropriate physical strength, a composition for the preparation that has an excellent tabletability, and a method for producing the same.

BACKGROUND ART

In a well-known administration method, a medicinal ingredient or an active ingredient is administered in the form of a tablet containing the ingredient. Particularly in the pharmaceutical field, various tablet-form pharmaceutical products have been widely used for treating or preventing a disease.

Also in several fields other than the pharmaceutical field, e.g. in the fields of FOSHU (Food for Specified Health Uses) and nutritional supplement, tablet-form products have been proposed in recent years. However, in general, a dose adequate to achieve a desired effect of an active ingredient in the nutritional supplement or the like is significantly larger than that of a medicinal ingredient in the pharmaceutical product. Therefore, for example, the user of the nutritional supplement or the like has to take in a larger-sized tablet or a larger number of tablets in a single dose, and thus bears a large intake burden.

The content of the active ingredient in the tablet may be increased to solve the above problem. However, the content of an auxiliary ingredient such as a binder is relatively reduced to cause a problem with poor tabletability, tablet breakage due to insufficient binding strength, or the like.

Use of a casein in a tablet is described e.g. in the following documents.

Patent Document 1 discloses a casein for use as a surface stabilizer in a process of tableting a composition containing an active nanoparticle ingredient. Patent Document 2 discloses a tablet confectionery containing a casein phosphopeptide as a bitterness inhibitor. Patent Document 3 discloses a coenzyme Q10 composition containing a casein and a saccharide other than polysaccharides, and further discloses a tablet containing the composition. However, in the documents, the caseins are used as auxiliary ingredients, and the tablets have remarkably low casein concentrations.

Meanwhile, Patent Document 4 discloses that a casein hydrolysate has an angiotensin converting enzyme inhibitory effect or a hypotensive effect, and Patent Document 5 discloses that a casein hydrolysate containing a particular peptide has a brain function improving effect.

Therefore, the casein hydrolysates have attracted much attention also as active ingredients due to the above effects.
Patent Document 1: JP 2013-209422 A
Patent Document 2: JP 2012-217442 A
Patent Document 3: WO 2009-001787 A
Patent Document 4: WO 2005-012542 A
Patent Document 5: JP 2013-5763 A

SUMMARY OF THE INVENTION

Problems to be Solved by the Invention

The casein hydrolysate contains a functional peptide having a physiological effect, and is expected to be used as a main ingredient in a tablet-form immediate-release preparation. However, in general, the functional peptide used as the active ingredient is present at a low concentration in the casein hydrolysate. Therefore, in the case of not performing a pretreatment such as a concentrating treatment, it is necessary to increase the number of the tablets or the size of the tablet in single dose in order to achieve a desired effective intake amount. However, the increase of the number or size leads to the increase of the intake burden on the user, and it is preferable to prevent such increase. The intake burden can be reduced directly and effectively by increasing the active ingredient concentration in the tablet.

However, the casein and the casein hydrolysate exhibit low tabletabilities. Therefore, the tablet requires a certain amount of an ingredient such as a binder, an excipient, or a lubricant for improving the tabletability, shape maintainability, or the like. Consequently, it is difficult to increase the active ingredient concentration in the tablet. The increase of the active ingredient concentration leads to decrease in the content of the other ingredient such as the binder, the excipient, or the lubricant. Thus, it is extremely difficult to achieve both of the intake burden reduction and the improved tabletability. There have been no reports on a tablet-form immediate-release preparation containing 50% or more of the active ingredient.

Accordingly, an object of the present invention is to provide a tablet-form immediate-release preparation that contains a high concentration (specifically 50% by mass or more) of a casein and/or a casein hydrolysate as an active ingredient but has an excellent physical strength.

In the specification, the term "immediate-release preparation" means a preparation for oral administration included in "preparations showing a release pattern of active substance(s) that is not intentionally modified" described in The Japanese Pharmacopoeia 16th edition. The term "tablet-form immediate-release preparation" means the immediate-release preparation having a tablet shape. Specifically, the tablet-form immediate-release preparation is a tablet that disintegrates within a prescribed time of 30 minutes (for a plain tablet) or 60 minutes (for a coated tablet) in the disintegration test according to The Japanese Pharmacopoeia 16th edition. The tablet-form immediate-release preparation of the present invention may be referred to simply as the tablet hereinafter.

Another object of the present invention is to provide a composition for the tablet-form immediate-release preparation that contains a high concentration (specifically 50% by mass or more) of the casein and/or the casein hydrolysate as an active ingredient but has an excellent tabletability.

A further object of the present invention is to provide a method capable of producing the tablet having the excellent property with a high production efficiency.

Means for Solving the Problem

As a result of intensive research in view of the above problem, the inventors have found that a composition having an excellent tabletability can be obtained by mixing a casein and/or a casein hydrolysate with a lactose having a particular volume average particle diameter, and have developed a method for tableting the composition and a tablet-form immediate-release preparation with an excellent physical strength. The present invention has been accomplished based on the finding.

According to an aspect of the present invention, there is provided a tablet-form immediate-release preparation, which contains 50% by mass or more of a casein and/or a casein hydrolysate, and further contains 6.0 to 100 parts by mass of a lactose per 100 parts by mass of the casein and/or the casein hydrolysate, the lactose having a volume average particle diameter of not less than 50 μm and not more than 300 μm.

According to another aspect of the present invention, there is provided a composition for the tablet-form immediate-release preparation, which contains 50% by mass or more of the casein and/or the casein hydrolysate, and further contains 6.0 to 100 parts by mass of the lactose per 100 parts by mass of the casein and/or the casein hydrolysate, the lactose having a volume average particle diameter of not less than 50 μm and not more than 300 μm.

According to a further aspect of the present invention, there is provided a method for producing the tablet-form immediate-release preparation comprising the steps of: preparing a mixture containing 50% by mass or more of the casein and/or the casein hydrolysate and 6.0 to 100 parts by mass of the lactose per 100 parts by mass of the casein and/or the casein hydrolysate, the lactose having a volume average particle diameter of not less than 50 μm and not more than 300 μm; filling a mortar with the mixture and tableting the mixture; and separating the tableted mixture from the mortar.

Effect of the Invention

The tablet-form immediate-release preparation of the present invention has an excellent physical strength since the lactose having a particular volume average particle diameter is added to the casein and/or the casein hydrolysate. The tablet contains a high concentration of the active ingredient, and thereby is capable of reducing an intake burden on a user.

The composition of the present invention has an excellent tabletability and can be processed into the tablet having an excellent physical strength since the lactose having a particular volume average particle diameter is added to the casein and/or the casein hydrolysate. The composition contains a high concentration of the active ingredient, and thereby is capable of reducing an intake burden on a user in the tablet.

The method of the present invention uses the composition of the present invention having an excellent tabletability, and thereby is capable of producing the tablet of the present invention with high production efficiency without tableting troubles. Furthermore, the method is capable of producing the tablet that contains a high concentration of the active ingredient, has an excellent binding strength between the ingredients, and has an excellent physical strength.

In the description, the term "the tablet has an excellent physical strength" means that the tablet passes the tablet friability test according to The Japanese Pharmacopoeia 16th edition as specifically described hereinafter in Examples.

The term "the composition has an excellent tabletability" means that tableting troubles such as capping, laminating, binding, and sticking are not caused in tablet production to be hereinafter described.

EMBODIMENTS OF THE INVENTION

The present invention will be described in more detail below.

In the present invention, a material for preparing the casein and/or the casein hydrolysate is not particularly limited, and may be an animal milk such as a cow's milk, sheep's milk, or goat's milk. The casein hydrolysate is not particularly limited, and may be produced under conditions suitable for obtaining a desired functional peptide or amino acid. For example, the casein hydrolysate may be an enzymatic decomposition product, a thermal decomposition product, an acid decomposition product, or the like, preferably an enzymatic hydrolysis product of a casein. The casein hydrolysate contains various functional peptides, and can be utilized for producing a high- or multi-functional tablet.

In the present invention, the caseins include casein-based materials approved as food additives such as casein sodium.

In the present invention, the casein hydrolysate may be selected from hydrolysates disclosed in WO 2005/012542, JP 2013-5763 A, etc. The casein hydrolysate disclosed in WO 2005/012542 is a highly decomposed product. The casein and/or the casein hydrolysate used in the present invention may contain an undecomposed casein or a highly decomposed casein hydrolysates.

WO 2005/012542 discloses an example of a solution containing an enzymatic decomposition product of a casein, which is obtained as follows: 1 g of a casein derived from a cow's milk is added to 99 g of a distilled water at about 80° C., the resultant is thoroughly stirred, a 1-N sodium hydroxide solution is added to adjust the pH to 7.0, the mixture is cooled to 20° C. to prepare a substrate solution, an enzyme derived from *Aspergillus oryzae* is added to the substrate solution so that the enzyme/casein ratio is 1/25 by weight, the casein is reacted at 50° C. for 14 hours, and the solution is subjected to autoclaving at 110° C. for 10 minutes to inactivate the enzyme. Examples of the enzymes include commercial products such as SUMIZYME (trademark) FP, CP, and RP available from Shin Nihon Chemical Co., Ltd., a trypsin available from Higuchi Inc., PROTEASE S available from Amano Enzyme Inc., a purified papain available from Nagase ChemteX Corporation, THERMOASE (trademark) available from Daiwa Fine Chemicals Co., Ltd., NEWRASE (trademark) F3G available from Amano Enzyme Inc., and a bromelain available from Shin Nihon Chemical Co., Ltd.

JP 2013-5763 A discloses an example of a peptide, which is obtained as follows: 10 mg of a casein sodium derived from a cow's milk is dispersed and dissolved in 1 ml of a phosphate buffer having a pH of 7.0 to 7.3, the resultant is heated to 50° C. to prepare a substrate solution, an enzyme containing a protease is added to the substrate solution so that the enzyme/casein ratio is 1/100 to 1/400 by weight, the casein sodium is reacted at 50° C. for 4 hours, and a 10% aqueous solution of trichloroacetic acid is added to the reaction solution at a final concentration of 1% to stop the reaction. Examples of the enzymes containing a protease include SUMIZYME (trademark) MP, FP, and LP50 available from Shin Nihon Chemical Co., Ltd., PROTEASE P5459 available from Sigma-Aldrich, and PROTEASE A "AMANO" SD, PROTEASE M "AMANO" SD, PROTEASE P "AMANO" 3SD, PROTEAX (trademark), UMAMIZYME G, PROTIN SD-AY10, PROTIN SD-NY10, THERMOASE (trademark) PC10F available from Amano Enzyme Inc.

The content of the casein and/or the casein hydrolysate is 50% by mass or more, preferably 55% by mass or more, based on the total mass of the tablet or the composition. It is preferred that the upper limit of the content is 90% by mass from the viewpoint of practicability such as tabletability of the composition. It is more preferred that the content is 80% by mass or less from the viewpoint of the physical strength of the tablet or the tabletability of the composition. When the content is 50% by mass or more, an intake burden on a user can be reduced.

In the present invention, a lactose acts as a binder and an excipient. In the present invention, the lactoses include lactose-based materials usable in food or pharmaceutical product such as lactose hydrates and anhydrous lactoses. The lactose is not particularly limited, and the lactose hydrate is preferred from the viewpoint of binding strength. Examples of the lactoses include commercial products such as DILACTOSE (trademark) available from Freund Corporation, LACTOSE GRANULE (trademark) available from Freund Corporation, TABLETTOSE (trademark) available from Meggle Japan Co., Ltd., FLOWLAC (trademark) available from Meggle Japan Co., Ltd., and SUNTOSE (trademark) EN available from Taiyo Kagaku Co., Ltd.

In the present invention, the lower limit of the volume average particle diameter of the lactose is 50 μm, and the upper limit thereof is 300 μm. When the volume average particle diameter is controlled within this range, the lactose can exhibit an excellent binding strength in an interaction with the casein and/or the casein hydrolysate, and the composition can be in a powder form suitable for tableting. When the volume average particle diameter is outside the range, the composition may fail to exhibit a sufficient tabletability, and the resultant tablet may be easily broken. In the present invention, the volume average particle diameter of the lactose is measured by a method according to "Laser Diffraction Measurement of Particle Size" described in The Japanese Pharmacopoeia 16th edition. For example, the volume average particle diameter may be measured by a laser diffraction-type particle size distribution measuring apparatus such as SALD-2300 available from Shimadzu Corporation, a laser diffraction/scattering-type particle size distribution measuring apparatus such as MT3100II available from Nikkiso Co., Ltd. or LA-9500 available from Horiba, Ltd., or the like. In this specification, the volume average particle diameter of the lactose is a value measured by the laser diffraction/scattering-type particle size distribution measuring apparatus LA-9500 under a dry condition at a refractive index of 1.6-0i, a wavelength of 655.0 nm, and a transmittance of 90% to 98%.

The lactose preferably has a repose angle of not less than 15° and not more than 45°. As for the lower limit, the repose angle is more preferably 20° or more, particularly preferably 25° or more. When the repose angle is within this range, the compatibility of the lactose with the active ingredient is improved, and the tabletability of the composition is further improved.

The repose angle may be measured by a method according to The Japanese Pharmacopoeia 16th edition. Specifically, a funnel is fixed above a horizontal base, a certain amount (about 200 g) of the lactose is supplied to the funnel at a rate of 20 to 60 g/minute, the diameter and height of a cone-like pile of the lactose transferred through the funnel onto the base are measured, and the base angle of the pile is calculated as the repose angle from the diameter and the height.

The content of the lactose is 6.0 to 100 parts by mass per 100 parts by mass of the casein and/or the casein hydrolysate. As for the lower limit, the content of the lactose is preferably 7 parts by mass or more, further preferably 19 parts by mass or more. As for the upper limit, the content of the lactose is preferably 96 parts by mass or less, further preferably 91 parts by mass or less. When the content is outside the above range, the composition may have an insufficient tabletability.

In general, tablets are required to have an appropriate physical strength to prevent breakage with time or due to an impact applied during the transportation.

The physical strength of the tablet of the present invention is such that the tablet disintegrates within 30 minutes (for a plain tablet) or 60 minutes (for a coated tablet) in the disintegration test according to The Japanese Pharmacopoeia 16th edition, and the tablet exhibits a maximum mean mass loss of 1.0% or less in the above tablet friability test. In the disintegration test, one tablet (sample) is placed in each of six glass tubes in a tester, the glass tubes are shaken at 37±2° C. in a constant temperature water tank at a rate of 29 to 32 cycle/minute through a distance of 53 to 57 mm, and the disintegration property of the tablet is observed. When the sample does not remain in the tester at all or does not keep the original shape, the sample is judged to be disintegrated.

The tablet of the present invention may contain one or more other ingredients if necessary in addition to the casein and/or the casein hydrolysate and the particular lactose, as long as the other ingredients do not inhibit the advantageous effects of the invention.

Examples of the other ingredients include lubricants, excipients other than the lactoses, binders, and other active ingredients.

It is preferred that the tablet of the present invention contains 2% by mass or more of a lubricant based on the total mass of the tablet from the viewpoint of performing the tableting effectively and efficiently. The upper limit of the content of the lubricant is not particularly limited as long as the content of the casein and/or the casein hydrolysate and the content of the lactose are within the above-described ranges respectively. The content of the lubricant is preferably 12% by mass or less, more preferably 5% by mass or less.

Examples of the lubricants include calcium stearate, magnesium stearate, stearic acid, stearyl alcohols, sugar esters such as sucrose fatty acid esters and glycerin fatty acid esters, vegetable fat powders, waxes such as white beeswaxes and hydrogenated fats, talcs, silicic acid, and silicon.

Examples of the excipients and binders other than the lactoses include saccharides such as starches, dextrins, gum arabic powders, glucose, and maltose, sugar alcohols such as maltitol and isomalt, and cellulose derivatives such as crystalline celluloses and hydroxypropylcelluloses.

Examples of the other active ingredients include vitamins, minerals, amino acids, tea extracts such as catechins and Tenchas (sweet tea extracts), glucosamines, chondroitins, extracts of plants such as saw palmetto and apples, polyphenols derived from grapes and apples, lactic acid bacteria, *Bacillus subtilis*, and yeasts.

A method for producing the tablet will be described below. In general, a tablet is produced by tableting a powdery or granular raw material composition. In this tableting, a trouble such as capping, laminating, sticking, or binding may be caused. The capping means that a cap-shaped fragment is peeled off from a tablet and transferred to an upper pestle of a tableting machine in a step of separating a mold from the tablet. The laminating means that a laminar fragment is peeled off from a side surface of a tablet. The sticking means that a scratch is formed on a surface of a tablet because an ingredient cannot be easily separated from a pestle. The binding means that a dischargeability (mold releasability) of a tablet is deteriorated because the tablet is bonded to a mortar.

In general, it is extremely important from the viewpoint of improving the efficiency and yield of tablet production that the type and content of each ingredient for a raw material composition are appropriately selected so that the composition has an excellent tabletability to prevent the above troubles.

Therefore, in the tablet production method of the present invention, the composition for the tablet-form immediate-release preparation of the present invention is used as the raw material. First, the active ingredient of the casein and/or the casein hydrolysate is mixed with the lactose having a predetermined volume average particle diameter and if necessary with the other ingredient such as the lubricant at an appropriate ratio. It is preferred that the casein and/or the casein hydrolysate and the other ingredient are each in a powder form before the mixing. Alternatively, the casein and/or the casein hydrolysate and the other ingredient may be mixed and then granulated.

The content of the active ingredient of the casein and/or the casein hydrolysate is 50% by mass or more, preferably 55% by mass or more, based on the total mass of the mixture. It is preferred that the upper limit of the content is 90% by mass from the viewpoint of practicability such as tabletability of the composition. It is more preferred that the content is 80% by mass or less from the viewpoint of the physical strength of the tablet or the tabletability of the composition.

The lower limit of the volume average particle diameter of the lactose for the mixture is 50 μm, and the upper limit thereof is 300 μm. When the volume average particle diameter is controlled within this range, the lactose can exhibit an excellent binding strength in an interaction with a peptide and/or an amino acid in the casein and/or the casein hydrolysate, and the mixture can be in a powder form suitable for tableting. When the volume average particle diameter is outside the range, the mixture may fail to exhibit a sufficient tabletability, and the resultant tablet may be broken.

The content of the lactose is 6.0 to 100 parts by mass per 100 parts by mass of the casein and/or the casein hydrolysate in the mixture. As for the lower limit, the content of the lactose is preferably 7 parts by mass or more, further preferably 19 parts by mass or more. As for the upper limit, the content of the lactose is preferably 96 parts by mass or less, further preferably 91 parts by mass or less. When the content is outside the above range, the tabletability of the mixture may be deteriorated.

It is preferred that the mixture contains 2% to 5% of the lubricant as the other ingredient. In this case, the tablet can be produced with more excellent moldability.

The mixing of the ingredients for the raw material is not particularly limited as long as the ingredients can be sufficiently mixed. The ingredients may be preferably mixed by using a powder mixing device such as a powder stirrer mixer, a double-cone mixer, a V-shaped mixer, a tumbler mixer, or a screw mixer.

A mortar of a tableting machine is filled with the mixture used as the composition for the tablet, and the mixture is tableted by a pestle at around room temperature. After the tableting, the formed tablet is discharged from the mortar of the tableting machine to obtain the tablet of the present invention. The tableting is carried out preferably in a dehumidified atmosphere or at a humidity of 60% or less. In this case, the tablet can be easily separated from the mold.

A pressure applied in the tableting is preferably 0.1 to 2.0 t. As for the lower limit, the pressure is more preferably 0.5 t or more. As for the upper limit, the pressure is more preferably 1.5 t or less. In this case, the produced tablet can exhibit an appropriate physical strength. When the lubricant is used as the ingredient for the tablet, the mold releasability of the tablet is further improved, and an excessive impact is not applied to the mortar and the pestle.

The type of the tableting machine is not particularly limited. For example, the tableting machine may be of a single punch type or a rotary type. The rotary type tableting machine is preferred from the viewpoint of continuous production.

The pestle and the mortar in the tableting machine usable in the present invention are not particularly limited, and may have a known shape.

In general, it is difficult to form a tablet having a shape with a small curvature radius. The tablet production method of the present invention is capable of forming without troubles even the tablet having the small curvature radius, such as a swallowing type tablet having a diameter of 9 mm and a curvature radius R (of a curved surface of the tablet) of 7 mm or a tablet having a diameter of 9 mm and a curvature radius R of 7.5 mm. A coating may be formed on the tablet to improve the storage stability or to mask the flavor. The coating can be formed without defects even in a case where the tablet has a shape unsuitable for the coating, e.g. a shape with a diameter of 9 mm and a large curvature radius R of 13 mm.

EXAMPLES

The present invention will be described below with reference to Examples without intension of restricting the invention.

<Ingredients for Raw Material>
Active Ingredient (Casein and/or Casein Hydrolysate)
(1) Powdery casein hydrolysate A (AMEAL PEPTIDE E-10 available from Calpis Co., Ltd.)
(2) Powdery casein hydrolysate B (prepared as follows: 10 mg of a casein sodium derived from a cow's milk was dispersed and dissolved in 1 ml of a phosphate buffer having a pH of 7.0 to 7.3, the resultant was heated to 50° C. to prepare a substrate solution, a commercially available enzyme PROTIN SD-AY10 available from Amano Enzyme Inc. was added to the substrate solution so that the enzyme/casein ratio was 1/1000 by mass, the casein sodium was reacted at 50° C. for 4 hours, and a 10% aqueous solution of trichloroacetic acid was added to the reaction solution at a final concentration of 1% to stop the reaction)
(3) Powdery casein sodium (TATUA (trademark) 100 available from Tatua)
Excipient (and Binder)
(1) Lactose 1: LACTOSE GRANULE (trademark) having a volume average particle diameters of 59, 162, 279, or 335 μm available from Freund Corporation
(2) Lactose 2: TABLETTOSE (trademark) 80 having a volume average particle diameter of 223 μm available from Meggle Japan Co., Ltd.

(3) Lactose 3: FLOWLAC (trademark) 100 having a volume average particle diameter of 136 μm available from Meggle Japan Co., Ltd.

(4) Lactose 4: SUNTOSE EN having a volume average particle diameter of 58 μm available from Taiyo Kagaku Co., Ltd.

(5) Lactose 5: SORBOLAC (trademark) 400 having an average particle diameter of 9 μm available from Meggle Japan Co., Ltd.

(6) Lactose 6: GRANULAC (trademark) 70 having a volume average particle diameter of 122 μm available from Meggle Japan Co., Ltd.

(7) Tapioca starch available from Matsutani Chemical Industry Co., Ltd.

(8) Starch: PERFILLER (trademark) 102 available from Freund Corporation (9) Dextrin: PINEDEX (trademark) #2AG available from Matsutani Chemical Industry Co., Ltd.

Lubricant: Calcium stearate available from Taihei Chemical Industrial Co., Ltd.

Others (anticaking agent): Silicon oxide SYLOPAGE (trademark) 720 available from Fuji Silysia Chemical Ltd.

<Tableting Machine and Tableting Condition>

Tablets were produced by using PICCOLA D/8 (φ 9 mm, R 7.5 mm, four pestle/mortar units) available from RIVA under a temperature of 20° C., a humidity of 40%, a tableting pressure of 1.5 t, and a rotation rate of 15 rpm.

<Tablet Evaluation>

1. Physical Strength

The physical strengths of the tablets were evaluated according to the tablet friability test described in The Japanese Pharmacopoeia 16th edition as follows.

A synthetic resin drum having an internal diameter of 283 to 291 mm and a depth (inside thickness) of 36 to 40 mm was used. A curved projection having an inside radius of 75.5 to 85.5 mm extended from the middle to the outer wall of the drum. The tablets having a total mass of approximately 6.5 g were placed in the drum. The drum was rotated 100 times at 25±1 rpm, and the tablets were collected. Dust attached to the tablets was removed, and the total mass of the tablets was measured accurately to obtain a mass decrease value. This test was carried out three times, and the average of three mass decrease values (the maximum mean mass loss) was calculated.

A: Cracking, cleavage, and breakage were not observed in the tablets, and the maximum mean mass loss was 1.0% or less (the tablets passed the friability test).

B: Cracking, cleavage, and breakage were not observed in the tablets, but the maximum mean mass loss was more than 1.0%.

C: Cracking, cleavage, or breakage was observed in the tablets.

2. Tabletability

A: Capping, laminating, sticking, and binding were not caused.

B: Capping, laminating, sticking, and binding were not caused, but the tablet did not have a lustered surface or a powder was readily attached to the mortar or pestle.

C: At least one trouble of capping, laminating, sticking, and binding was caused.

Example 1

50.0% by mass of Powdery casein hydrolysate A, 45.5% by mass of Lactose 1 having an average particle diameter of 162 μm, 3.0% by mass of the calcium stearate, and 1.5% by mass of the silicon oxide were mixed in a dry powder mixer RM-10-2 available from Aichi Electric Co., Ltd. The resultant mixture was directly tableted by the above tableting machine under a tableting pressure of 1.5 t to produce 500 round tablets each having a mass of 350 mg.

The physical strength and the tabletability of the produced tablets were evaluated in the above manner. The results are shown in Table 1.

Examples 2 to 7

500 round tablets each having a mass of 350 mg were produced in each example in the same manner as Example 1 except that the contents of Powdery casein hydrolysate A, Lactose 1 having an average particle diameter of 162 μm, the lubricant, and the other ingredients were changed as shown in Table 1. The produced tablets were evaluated in the same manner as Example 1. The results are shown in Table 1.

Comparative Example 1

500 round tablets each having a mass of 350 mg were produced in the same manner as Example 1 except that the content of Powdery casein hydrolysate A was changed to 95.5% by mass and Lactose 1 was not added. The produced tablets were evaluated in the same manner as Example 1. The results are shown in Table 1.

Comparative Examples 2 and 3

500 round tablets each having a mass of 350 mg were produced in each example in the same manner as Example 1 except that the contents of Powdery casein hydrolysate A, Lactose 1 having an average particle diameter of 162 μm, and the lubricant were changed as shown in Table 1 and the silicon oxide was not added. The produced tablets were evaluated in the same manner as Example 1. The results are shown in Table 1.

Comparative Examples 4 and 5

500 round tablets each having a mass of 350 mg were produced in each example in the same manner as Example 1 except that the tapioca starch or PERFILLER (trademark) 102 and PINEDEX (trademark) #2AG were used instead of Lactose 1 and the contents of these ingredients and Powdery casein hydrolysate A were changed as shown in Table 1. The produced tablets were evaluated in the same manner as Example 1. The results are shown in Table 1.

Examples 8 and 9

500 round tablets each having a mass of 350 mg were produced in each example in the same manner as Example 2 except for using Lactose 2 or 3 instead of Lactose 1 having an average particle diameter of 162 μm. The produced tablets were evaluated in the same manner as Example 1. The results are shown in Table 2.

Example 10

500 round tablets each having a mass of 350 mg were produced in the same manner as Example 1 except that Lactose 1 was screened through a metal screen having an opening of 63 μm (250 mesh) to obtain particles having an average particle diameter of 59 μm. The produced tablets were evaluated in the same manner as Example 1. The results are shown in Table 2.

Example 11

500 round tablets each having a mass of 350 mg were produced in the same manner as Example 1 except that Lactose 1 was screened through a metal screen having an opening of 250 μm (60 mesh) or 300 μm (50 mesh) to obtain particles having an average particle diameter of 279 μm. The produced tablets were evaluated in the same manner as Example 1. The results are shown in Table 2.

Example 12

500 round tablets each having a mass of 350 mg were produced in the same manner as Example 1 except for using Lactose 4 instead of Lactose 1. The produced tablets were evaluated in the same manner as Example 1. The results are shown in Table 2.

Comparative Example 6

500 round tablets each having a mass of 350 mg were produced in the same manner as Example 1 except that Lactose 1 was screened through a metal screen having an opening of 250 μm (60 mesh) or (50 mesh) to obtain particles having an average particle diameter of 335 μm. The produced tablets were evaluated in the same manner as Example 1. The results are shown in Table 2.

Comparative Examples 7 and 8

500 round tablets each having a mass of 350 mg were produced in each example in the same manner as Example 1 except for using Lactose 5 or 6 instead of Lactose 1. The produced tablets were evaluated in the same manner as Example 1. The results are shown in Table 2.

Example 13

500 round tablets each having a mass of 350 mg were produced in the same manner as Example 2 except for using Powdery casein hydrolysate B instead of Powdery casein hydrolysate A. The produced tablets were evaluated in the same manner as Example 1. The results are shown in Table 3.

Example 14

500 round tablets each having a mass of 350 mg were produced in the same manner as Example 2 except for using the powdery casein sodium instead of Powdery casein hydrolysate A. The produced tablets were evaluated in the same manner as Example 1. The results are shown in Table 3.

TABLE 1

|  |  | Ex. 1 | Ex. 2 | Ex. 3 | Ex. 4 | Ex. 5 | Ex. 6 | Ex. 7 | Comp. Ex. 1 | Comp. Ex. 2 | Comp. Ex. 3 | Comp. Ex. 4 | Comp. Ex. 5 |
|---|---|---|---|---|---|---|---|---|---|---|---|---|---|
| Tablet composition (% by mass) | Powdery casein hydrolysate A | 50.0 | 55.0 | 62.0 | 75.5 | 80.0 | 90.0 | 50.0 | 95.5 | 90.0 | 92.0 | 62.0 | 62.5 |
|  | Lactose 1 | 45.5 | 40.5 | 33.5 | 20.0 | 15.5 | 7.0 | 48.0 | — | 5.0 | 5.0 | — | — |
|  | Tapioca starch | — | — | — | — | — | — | — | — | — | — | 33.5 | — |
|  | PERFILLER 102 | — | — | — | — | — | — | — | — | — | — | — | 20.0 |
|  | PINEDEX # 2AG | — | — | — | — | — | — | — | — | — | — | — | 13.0 |
|  | Calcium stearate | 3.0 | 3.0 | 3.0 | 3.0 | 3.0 | 3.0 | 2.0 | 3.0 | 5.0 | 3.0 | 3.0 | 3.0 |
|  | Silicon oxide | 1.5 | 1.5 | 1.5 | 1.5 | 1.5 | — | — | 1.5 | — | — | 1.5 | 1.5 |
| Volume average particle diameter of lactose (μm) |  | 162 | 162 | 162 | 162 | 162 | 162 | 162 | — | 162 | 162 | — | — |
| Repose angle of lactose (°) |  | 38 | 38 | 38 | 38 | 38 | 38 | 38 | — | 38 | 38 | — | — |
| Evaluation | Physical strength | A | A | A | A | A | A | A | C | C | C | C | C |
|  | Tabletability | A | A | A | A | A | A | A | A | A | A | A | C |

TABLE 2

|  |  | Ex. 8 | Ex. 9 | Ex. 10 | Ex. 11 | Ex. 12 | Comp. Ex. 6 | Comp. Ex. 7 | Comp. Ex. 8 |
|---|---|---|---|---|---|---|---|---|---|
| Tablet composition (% by mass) | Powdery casein hydrolysate A | 55.0 | 55.0 | 50.0 | 50.0 | 50.0 | 50.0 | 50.0 | 50.0 |
|  | Lactose 1 | — | — | 45.5 | 45.5 | — | 45.5 | — | — |
|  | Lactose 2 | 40.5 | — | — | — | — | — | — | — |
|  | Lactose 3 | — | 40.5 | — | — | — | — | — | — |
|  | Lactose 4 | — | — | — | — | 45.5 | — | — | — |
|  | Lactose 5 | — | — | — | — | — | — | 45.5 | — |
|  | Lactose 6 | — | — | — | — | — | — | — | 45.5 |
|  | Calcium stearate | 3.0 | 3.0 | 3.0 | 3.0 | 3.0 | 3.0 | 3.0 | 3.0 |
|  | Silicon oxide | 1.5 | 1.5 | 1.5 | 1.5 | 1.5 | 1.5 | 1.5 | 1.5 |
| Volume average particle diameter of lactose (μm) |  | 223 | 136 | 59 | 279 | 58 | 335 | 9 | 122 |
| Repose angle of lactose (°) |  | 34 | 28 | 41 | 41 | 43 | 45 | 52 | 46 |
| Evaluation | Physical strength | A | A | A | A | A | C | C | C |
|  | Tabletability | A | A | A | A | A | C | C | C |

TABLE 3

|  |  | Ex. 13 | Ex. 14 |
| --- | --- | --- | --- |
| Tablet composition (% by mass) | Powdery casein hydrolysate B | 55.0 | — |
|  | Powdery casein sodium | — | 55.0 |
|  | Lactose 1 | 40.5 | 40.5 |
|  | Calcium stearate | 3.0 | 3.0 |
|  | Silicon oxide | 1.5 | 1.5 |
| Volume average particle diameter of lactose (μm) |  | 162 | 162 |
| Repose angle of lactose (°) |  | 38 | 38 |
| Evaluation | Physical strength | A | A |
|  | Tabletability | A | A |

As is clear from Tables 1 to 3, the tablets of Examples 1 to 14 exhibit higher binding strengths of the ingredients and higher physical strengths significantly as compared with the tablets of Comparative Examples. Furthermore, the compositions of Examples 1 to 14 have more excellent tabletabilities, resulting in higher production efficiencies. In addition, the tablets of Examples 1 to 14 have higher active ingredient contents, and thereby are capable of reducing an intake burden on a user.

What is claimed is:

1. A tablet-form immediate-release preparation comprising
   50% by mass or more of a casein and/or a casein hydrolysate and
   6.0 to 100 parts by mass of a lactose per 100 parts by mass of the casein and/or the casein hydrolysate,
   the lactose having a volume average particle diameter of not less than 50 μm and not more than 300 μm.

2. The tablet-form immediate-release preparation according to claim 1, wherein the casein and/or the casein hydrolysate contains an enzymatic decomposition product of a casein.

3. The tablet-form immediate-release preparation according to claim 1, wherein the lactose has a repose angle of 15° to 45°.

4. The tablet-form immediate-release preparation according to claim 1, further comprising 2% by mass or more of a lubricant.

5. A composition for a tablet-form immediate-release preparation comprising
   50% by mass or more of a casein and/or a casein hydrolysate and
   6.0 to 100 parts by mass of a lactose per 100 parts by mass of the casein and/or the casein hydrolysate,
   the lactose having a volume average particle diameter of not less than 50 μm and not more than 300 μm.

6. The composition according to claim 5, wherein the casein and/or the casein hydrolysate contains an enzymatic decomposition product of a casein.

7. The composition according to claim 5, wherein the lactose has a repose angle of 15° to 45°.

8. The composition according to claim 5, further comprising 2% by mass or more of a lubricant.

9. A method for producing a tablet-form immediate-release preparation comprising the steps of:
   preparing a mixture containing 50% by mass or more of a casein and/or a casein hydrolysate and 6.0 to 100 parts by mass of a lactose per 100 parts by mass of the casein and/or the casein hydrolysate, the lactose having a volume average particle diameter of not less than 50 μm and not more than 300 μm;
   filling a mortar with the mixture and tableting the mixture; and
   separating the tableted mixture from the mortar.

10. The method according to claim 9, wherein the mixture further contains 2% by mass or more of a lubricant.

11. The method according to claim 9, wherein the casein and/or the casein hydrolysate is granulated before the step of preparing the mixture.

12. The method according to claim 10, wherein the casein and/or the casein hydrolysate and the lubricant are mixed and granulated before the step of preparing the mixture.

13. The method according to claim 9, wherein the mixture is in a powder form.

* * * * *